(12) United States Patent
Ning et al.

(10) Patent No.: US 10,504,991 B2
(45) Date of Patent: Dec. 10, 2019

(54) BIOSENSOR BASED ON HETEROJUNCTION BIPOLAR TRANSISTOR

(71) Applicant: INTERNATIONAL BUSINESS MACHINES CORPORATION, Armonk, NY (US)

(72) Inventors: Tak Ning, Yorktown Heights, NY (US); Sufi Zafar, Briarcliff Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 85 days.

(21) Appl. No.: 15/705,319

(22) Filed: Sep. 15, 2017

(65) Prior Publication Data

US 2018/0006116 A1 Jan. 4, 2018

Related U.S. Application Data

(63) Continuation of application No. 14/743,527, filed on Jun. 18, 2015, now Pat. No. 9,806,151, which is a
(Continued)

(51) Int. Cl.
*H01L 29/08* (2006.01)
*G01N 27/414* (2006.01)
(Continued)

(52) U.S. Cl.
CPC ..... *H01L 29/0817* (2013.01); *G01N 27/4145* (2013.01); *H01L 21/8222* (2013.01);
(Continued)

(58) Field of Classification Search
CPC ............. H01L 29/0817; H01L 29/6625; H01L 29/66318; H01L 27/082; H01L 27/1022;
(Continued)

(56) References Cited

U.S. PATENT DOCUMENTS 5,239,550 A    8/1993   Jain
5,665,614 A *   9/1997   Hafizi ............... H01L 29/66318
                                                                  257/197
(Continued)

OTHER PUBLICATIONS

Greenburg, R. et al, "Noise Performance of Low Base Resistance 200 GHz SiGe Technology", Tech. Digest of the IEEE IEDM, 2002, pp. 787-790.
(Continued)

*Primary Examiner* — Eduardo A Rodela
(74) *Attorney, Agent, or Firm* — Kristofer L. Haggerty

(57) ABSTRACT

In one example, a sensor includes a heterojunction bipolar transistor and component sensing surface coupled to the heterojunction bipolar transistor via an extended base component. In another example, a biosensor for detecting a target analyte includes a heterojunction bipolar transistor and a sensing surface. The heterojunction bipolar transistor includes a semiconductor emitter including an emitter electrode for connecting to an emitter voltage, a semiconductor collector including a collector electrode for connecting to a collector voltage, and a semiconductor base positioned between the semiconductor emitter and the semiconductor collector. The sensing surface is coupled to the semiconductor base of the heterojunction bipolar transistor via an extended base component and includes a conducting film and a reference electrode.

17 Claims, 4 Drawing Sheets

FIG. 1

Related U.S. Application Data continuation of application No. 14/739,456, filed on Jun. 15, 2015, now abandoned.

(60) Provisional application No. 62/090,390, filed on Dec. 11, 2014.

(51) Int. Cl.
| | |
|---|---|
| *H01L 29/165* | (2006.01) |
| *H01L 29/737* | (2006.01) |
| *H01L 29/10* | (2006.01) |
| *H01L 29/205* | (2006.01) |
| *H01L 21/8222* | (2006.01) |
| *H01L 29/423* | (2006.01) |
| *H01L 29/06* | (2006.01) |

(52) U.S. Cl.
CPC ...... *H01L 29/0649* (2013.01); *H01L 29/0804* (2013.01); *H01L 29/0821* (2013.01); *H01L 29/1004* (2013.01); *H01L 29/1008* (2013.01); *H01L 29/165* (2013.01); *H01L 29/205* (2013.01); *H01L 29/42304* (2013.01); *H01L 29/737* (2013.01); *H01L 29/7371* (2013.01)

(58) Field of Classification Search
CPC ........... H01L 27/11801; H01L 27/2445; H01L 29/0804; H01L 29/10; H01L 29/1004; H01L 29/423; H01L 29/42304
See application file for complete search history.

(56) References Cited

U.S. PATENT DOCUMENTS

| | | |
|---|---|---|
| 6,287,776 B1 | 9/2001 | Hefti |
| 6,346,453 B1 | 2/2002 | Kovacic |
| 8,858,782 B2 | 10/2014 | Fife |
| 2003/0080349 A1* | 5/2003 | Quaglietta .......... H01L 23/4821 257/197 |
| 2004/0149994 A1* | 8/2004 | Yi ....................... H01L 29/0817 257/79 |
| 2004/0185591 A1* | 9/2004 | Hsiung ................ G01N 27/414 438/49 |
| 2006/0065936 A1 | 3/2006 | Kerr |
| 2008/0083934 A1* | 4/2008 | Pagette ............... H01L 29/0821 257/197 |
| 2008/0220535 A1 | 9/2008 | LeBoefu |
| 2008/0230807 A1* | 9/2008 | Kuroda ................ H01L 23/367 257/197 |
| 2013/0221406 A1 | 8/2013 | Gaska |
| 2014/0030819 A1* | 1/2014 | Rajagopal ............... H01L 29/73 436/501 |
| 2014/0097910 A1 | 4/2014 | Breslin |
| 2014/0159129 A1 | 6/2014 | Wang |
| 2014/0264341 A1* | 9/2014 | Camillo-Castillo ........................ H01L 21/7624 257/49 |
| 2016/0011216 A1 | 1/2016 | Feller |

OTHER PUBLICATIONS

Greenburg, R. et al., "Noise Performance Scaling in High-Speed Silicon RF Technologies", Silicon Monolithic Integrated Circuits in RF, 2003, pp. 2-25.

Niu G. et al., "Noise-gain tradeoff in RD SiGe HBTs", IEEE Journal of Solid-State Electronics 46, Jan. 2002, pp. 1445-1451.

Milosev, I. et al. "Comparison of TiN, ZrN and CrN hard nitride coatings: Electrochemical and thermal oxidation", Thin Solid Films 303, 1997, pp. 246-254.

* cited by examiner

BIOSENSOR BASED ON HETEROJUNCTION BIPOLAR TRANSISTOR

FIELD OF THE DISCLOSURE

The present disclosure relates generally to analytical devices and relates more specifically the biosensors.

BACKGROUND OF THE DISCLOSURE

Biosensors combine biological components with physicochemical detectors to detect analytes (i.e., chemical constituents that are of interest in an analytical procedure, such as ions and bio-molecules). As such, biosensors play an important role in environmental applications and in industries such as the food and healthcare fields. For example, some common examples of biosensors include blood glucose monitors and devices for detecting heavy metal ions and other contaminants in river water.

SUMMARY OF THE DISCLOSURE

In one example, a sensor includes a heterojunction bipolar transistor and component sensing surface coupled to the heterojunction bipolar transistor via an extended base component.

In another example, a biosensor for detecting a target analyte includes a heterojunction bipolar transistor and component sensing surface. The heterojunction bipolar transistor includes a semiconductor emitter including an emitter electrode for connecting to an emitter voltage, a semiconductor collector including a collector electrode for connecting to a collector voltage, and a semiconductor base positioned between the semiconductor emitter and the semiconductor collector. The sensing surface is coupled to the semiconductor base of the heterojunction bipolar transistor via an extended base component and includes a conducting film and a reference electrode.

BRIEF DESCRIPTION OF THE DRAWINGS

The teachings of the present disclosure can be readily understood by considering the following detailed description in conjunction with the accompanying drawings, in which.

To facilitate understanding, identical reference numerals have been used, where possible, to designate identical elements that are common to the Figures.

DETAILED DESCRIPTION

Examples of the present disclosure provide a biosensor based on a heterojunction bipolar transistor. In one example, the biosensor comprises a heterojunction bipolar transistor (HBT) having a silicon germanium (SiGe) base that is connected, via an extended base component (e.g., a base bond pad and wire), to a sensing surface formed from a conducting film and a reference electrode. Like biosensors based on other types of transistors, the disclosed biosensor is capable of simultaneous temperature measurement and is compatible with complementary metal-oxide-semiconductor (CMOS) fabrication. However, the disclosed biosensor also provides additional advantages including improved long-term reliability of the sensing surface (due to decreased electrochemical reactions that degrade the sensing surface over time) and a lower limit of detection (due to higher signal-to-noise ratio).

Figure 1:
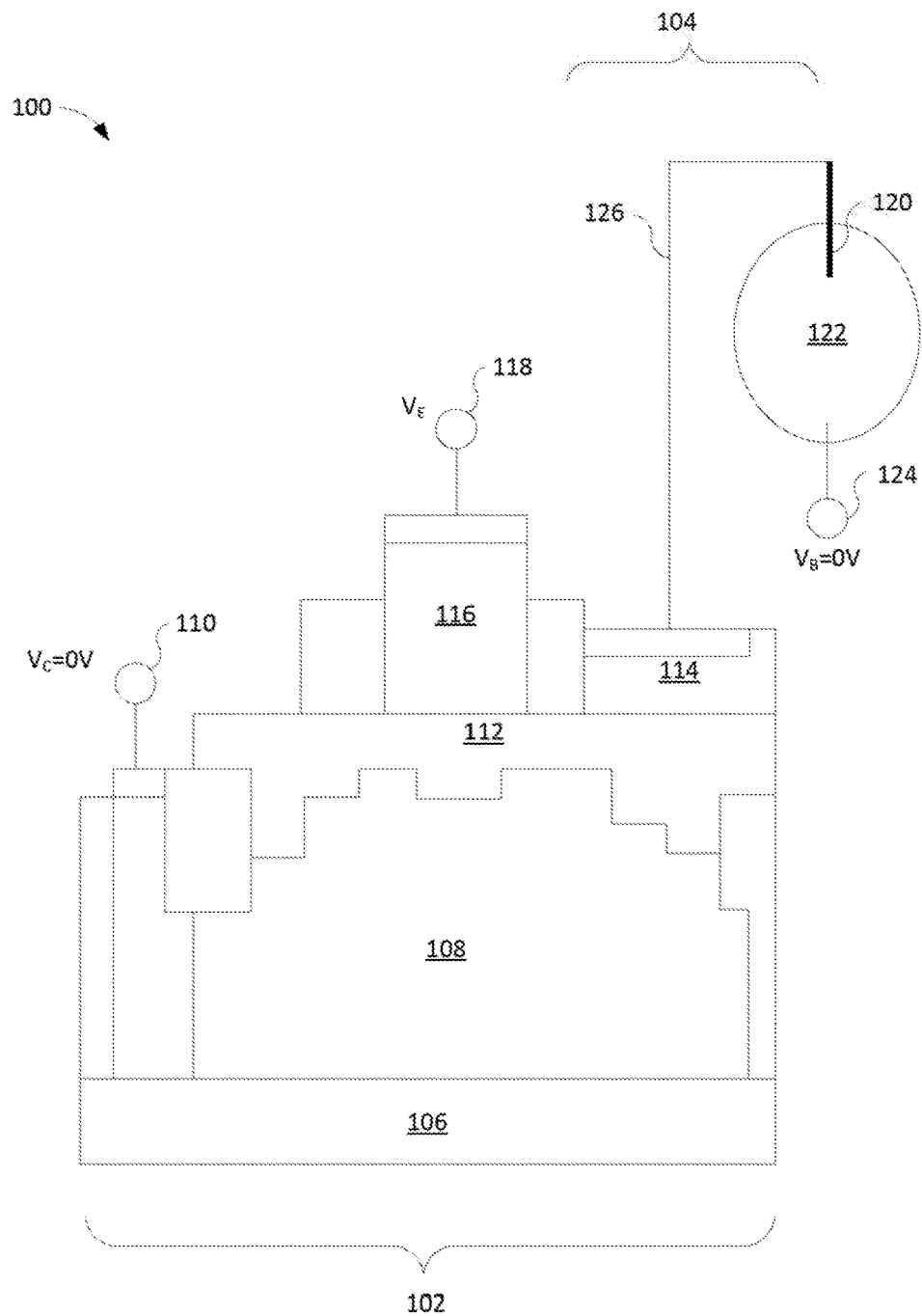
FIG. 1 is a cross sectional view illustrating a biosensor according to one example of the present invention.

FIG. 1 is a cross sectional view illustrating a biosensor 100 according to one example of the present invention. As illustrated, the biosensor 100 generally comprises a heterojunction bipolar transistor (HBT) device 102 coupled, via an extended base 104, to a sensing surface 120. The illustrated HBT device 102 is configured as an NPN device; however, it could alternatively be configured as a PNP device.

The HBT device 102 is fabricated upon a substrate 106, which in one example comprises doped silicon (Si). For example, the substrate 106 may comprise P-type doped (P) silicon.

A semiconductor collector (or "collector") 108 is formed on the substrate 106. In one example, the collector 108 also comprises silicon; however, the silicon is heavily doped (i.e., more heavily doped than the substrate 106, which may not be doped at all) and has a dopant polarity that is opposite to that of the substrate 106. For example, if the substrate 106 comprises P-type silicon, then the collector 108 comprises N-type heavily doped ($N^+$) silicon. Alternatively, the collector could comprise N-type heavily doped gallium arsenide (GaAs). The collector 108 includes a collector electrode 110 that can be connected to a collector voltage, $V_C$.

The semiconductor base (or "base") 112 of the HBT device 102 is formed on the collector 108. In one example, the base 112 comprises silicon germanium (SiGe). In a further example, the silicon germanium is heavily doped (i.e., more heavily doped than the substrate 106, but having a dopant concentration that may be similar to the doping concentration of the collector 108) and has a dopant polarity that is opposite to that of the collector 108. For example, if the collector 108 comprises N-type heavily doped silicon, then the base 112 comprises P-type heavily doped ($P^+$) silicon germanium.

The semiconductor emitter (or "emitter") 116 of the HBT device 102 is formed on the base 112. In one example, the emitter 116 comprises polysilicon or gallium arsenide. In a further example, the polysilicon is very heavily doped (i.e., doped more heavily than the collector 108 or the base 112) and has a dopant polarity that is opposite to that of the base 112. For example, if the base 112 comprises P-type heavily doped silicon germanium, then the emitter 116 comprises N-type very heavily doped ($N^{++}$) polysilicon. Alternatively, if the collector 108 comprises N-type heavily doped gallium arsenide and the base comprises P-type heavily doped gallium arsenide, then the emitter could comprise N-type very heavily doped gallium arsenide. The emitter 116 includes an emitter electrode 118 that can be connected to an emitter voltage $V_E$.

In one example, the extended base 104 comprises a base bond pad 114 and a conducting wire 126. For example, if the base 112 comprises P-type heavily doped ($P^+$) silicon germanium, then the base bond pad 114 may comprise P-type heavily doped ($P^+$) silicon which is silicided at the top. In an alternative example, the conducting film 120 is connected to the base bond pad 114 via a conducting wire.

As discussed above, the extended base 104 couples the HBT device 102 to a sensing surface comprised of a conducting film 120. The conducting film 120 is immersed in an aqueous solution 122 containing the target analyte. In one example, the aqueous solution further comprises water and dissolved salts (e.g., sodium chloride). In one example, the aqueous solution covers more than seventy percent of the conducting film's area. In one example, the conducting film 120 has a thickness of greater than one hundred nanometers. In a further example, the area of the conducting film 120 is much larger than the area of the emitter 116.

The conducting film 120 may comprise one or more of a variety of materials, where the materials are selected based upon the analyte that the biosensor 100 is designed to detect. For instance, if the biosensor 100 is designed to sense pH, then, then the conducting film 120 might be formed from titanium nitride (TiN) that is stoichiometric and contains no impurities (e.g., carbon); if the biosensor 100 is designed to detect bio-molecules and/or ions other than pH, then the conducting film 120 might be formed from functionalized conducting metal (e.g., such as titanium nitride, gold, or platinum); if the biosensor 100 is designed to sense chloride ions, then the conducting film 120 might be formed from a silver (Ag) film coated with one or more monolayers of silver chloride (AgCl) (e.g., such that the silver chloride is in direct contact with the aqueous solution); or if the biosensor 100 is designed to detect thiolated bio-molecules, then the conducting film 120 might be formed from gold (Au). The conducting film 120 can have a planar shape or a three-dimensional shape.

The sensing surface also includes a reference electrode 124 immersed in the aqueous solution, which can be connected to a reference voltage $V_B$.

As discussed above, the conducting film 120 may be connected to the base bond pad 114 via a wire 126. However, in an alternative example, the conducting film 120 is directly deposited over the base bond pad 114 (i.e., in this case, the extended base 104 comprises only the base bond pad 114). In this case, the conducting film 120 can be the same size or larger than the base bond pad 114. The conducting film 120 can also have a wire shape, a planar shape (e.g., flat), or a three-dimensional shape (e.g., pillar or surface of a trench).

The example biosensor 100 of FIG. 1, including an HBT device with a silicon germanium base, has demonstrated significantly higher gain (i.e., the ratio of collector current, $I_C$, to base current, $I_B$) and lower 1/f noise (or "pink noise") than other types of biosensors. These features result in improved sensing ability.

Figure 2B:
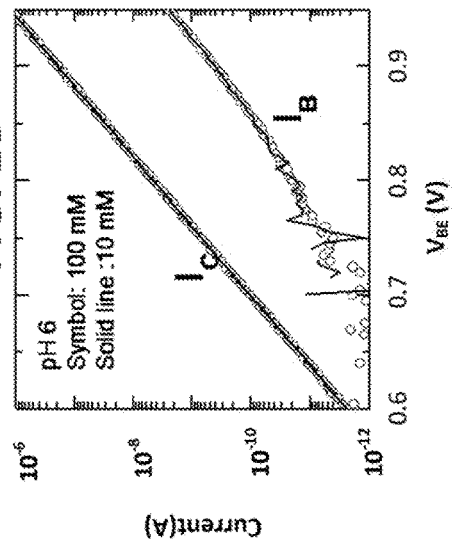
FIGS. 2A-2C consist of a plurality of charts plotting the collector current, $I_C$, and the base current, $I_B$, for an example heterojunction bipolar transistor-based sensor that is configured to sense pH, for a variety of pH values.
Figure 2A:
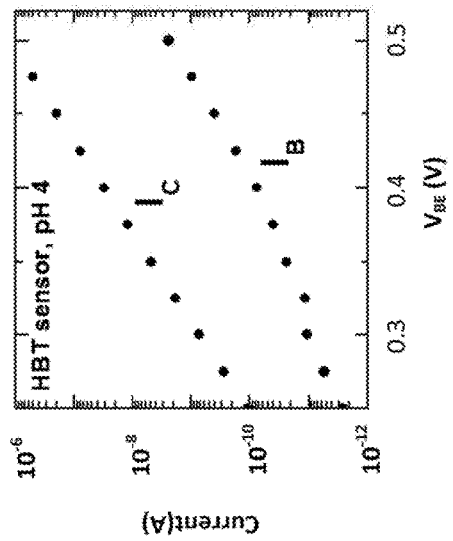
Figure 2C:
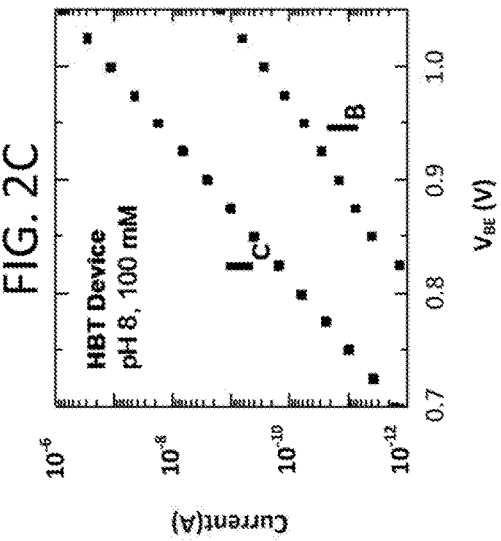

FIGS. 2A-2C, for example, consist of a plurality of charts plotting the measured collector current, $I_C$, and the measured base current, $I_B$, for an example heterojunction bipolar transistor-based sensor that is configured to sense pH, for a variety of pH values. In particular, FIG. 2A plots the collector current and base current of the HBT-based sensor when a pH of four is detected; FIG. 2B plots the collector current and base current of the HBT-based sensor when a pH of six is detected; and FIG. 2C plots the collector current and base current of the HBT-based sensor when a pH of eight is detected. The HBT-based sensor may be configured in the manner similar to the biosensor 100 illustrated in FIG. 1. In this case, the conducting film of the extended base may comprise, for example, titanium nitride.

The charts presented in FIGS. 2A-2C show that the gain for the HBT-based sensor is approximately 420, and that the base current is less than $2\times10^{-9}$ amperes. By contrast, the gain of a typical bipolar junction transistor is approximately fifty, and the base current is generally higher. The lower base current of the disclosed HBT-based sensor translated into a plurality of advantages.

For instance, the lower base current results in more accurate sensing and a wider sensing range. Consider that $I_BR$ is the voltage drop in the aqueous solution, due to the base current $I_B$ flowing through the solution during a measurement. The voltage drop $I_BR$ impacts the sensing signal (i.e., collector current $I_C$) as shown by the following transfer curve equation:

$$I_C = I_o \exp\{q(V_B + \psi_S - I_BR - V_E)/kT\} \quad \text{(EQN. 1)}$$

where $\psi_S$ is the sensing surface potential due to the bound analyte, is a measure of the target analyte concentration, and can be accurately measured provided $(I_BR) \ll kT/q$ ($\sim 1$ mV). $I_o$ is a constant, $V_B$ is the base voltage, $V_E$ is the emitter voltage, $q=1.6\times10^{-19}$ is the electronic charge, $k=1.38\times10^{-23}$ is the Boltzmann's constant, and T is Kelvin temperature. Lower voltage drops result in more accurate sensing (less error) over a wider dynamic range relative to sensors based on other types of transistors.

Additionally, lower base current results in better long-term chemical stability of the conducting film portion of the extended base. The base current causes electrochemically-induced changes in the conducting film, particularly after repeated use. More specifically, degradation of the conducting film depends on the base current density and can negatively impact the reliability of the sensor's readings. Thus, a lower base current slows degradation of the conducting film and improves the long-term reliability of the sensor.

As discussed above, the biosensor 100 of FIG. 1, including an HBT device with a silicon germanium base, has also demonstrated lower 1/f noise than other types of biosensors, as well as higher transconductance ($g_m$).

Figure 3B:
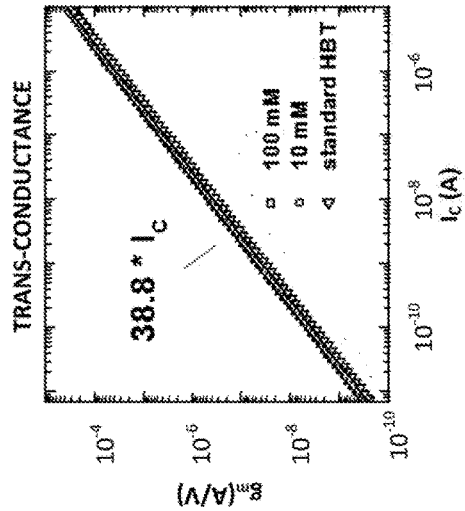
FIGS. 3A-3C consist of a plurality of charts plotting various noise characteristics of an example heterojunction bipolar transistor device against the collector current.
Figure 3A:
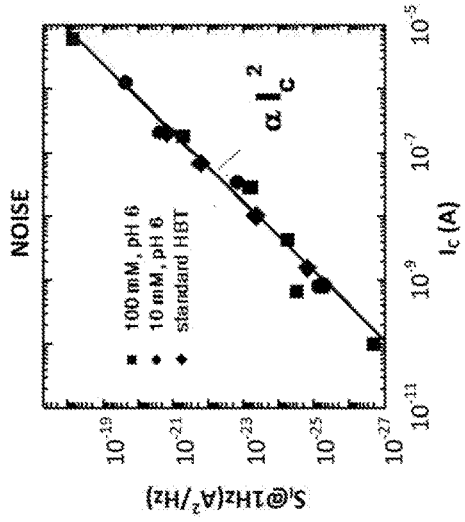
Figure 3C:
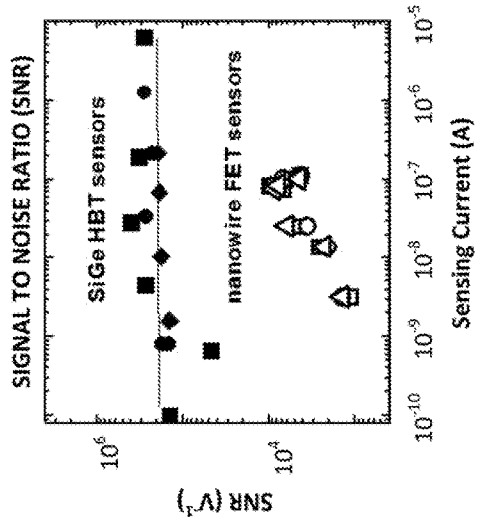

FIGS. 3A-3C, for example, consist of a plurality of charts plotting various noise characteristics of an example heterojunction bipolar transistor device against the collector (sensing) current, $I_C$. In particular, FIG. 3A plots the noise against the collector current; FIG. 3B plots the transconductance against the collector current; and FIG. 3C plots the signal-to-noise ratio (SNR) against the collector current, for an HBT-based sensor with a silicon germanium base and for a nanowire field effect transistor (FET)-based sensor.

The charts presented in FIGS. 3A-3B demonstrate lower 1/f noise and higher transconductance than is typical of devices based on other types of transistors. Lower 1/f noise and higher transconductance result in improved sensing characteristics. Moreover, the SNR, which can be defined as the transconductance divided by the square root of the 1/f noise (i.e., SNR=$g_m/\sqrt{S_I}$), is measured as approximately $2\times10^5$, which is among the highest reported SNR values for transistor-based sensors. Higher SNR implies higher resolution, and as shown in FIGS. 3A-3C is attributable to higher transconductance and lower 1/f noise for an HBT device having a silicon germanium base.

Figure 4A:
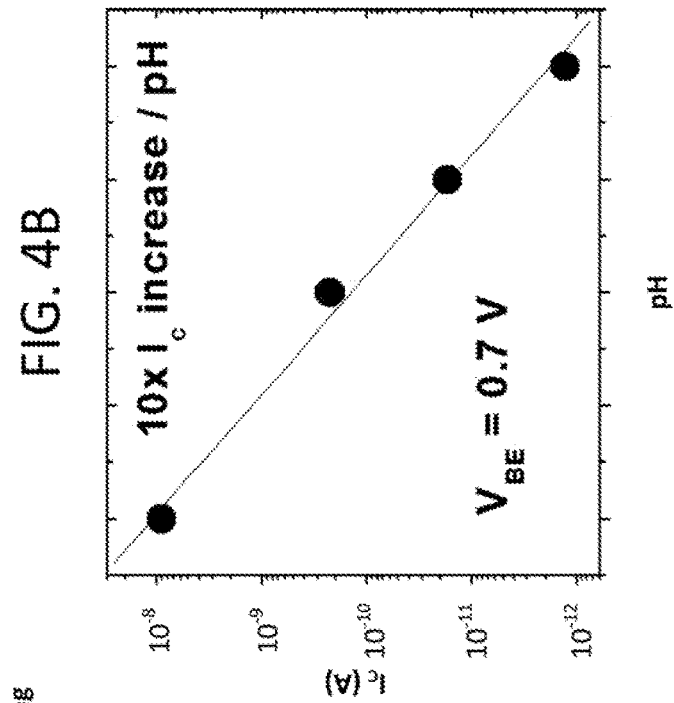
FIGS. 4A-4B consist of a plurality of charts illustrating the sensitivity of an example heterojunction bipolar transistor-based biosensor that is configured as a pH sensor.
Figure 4B:
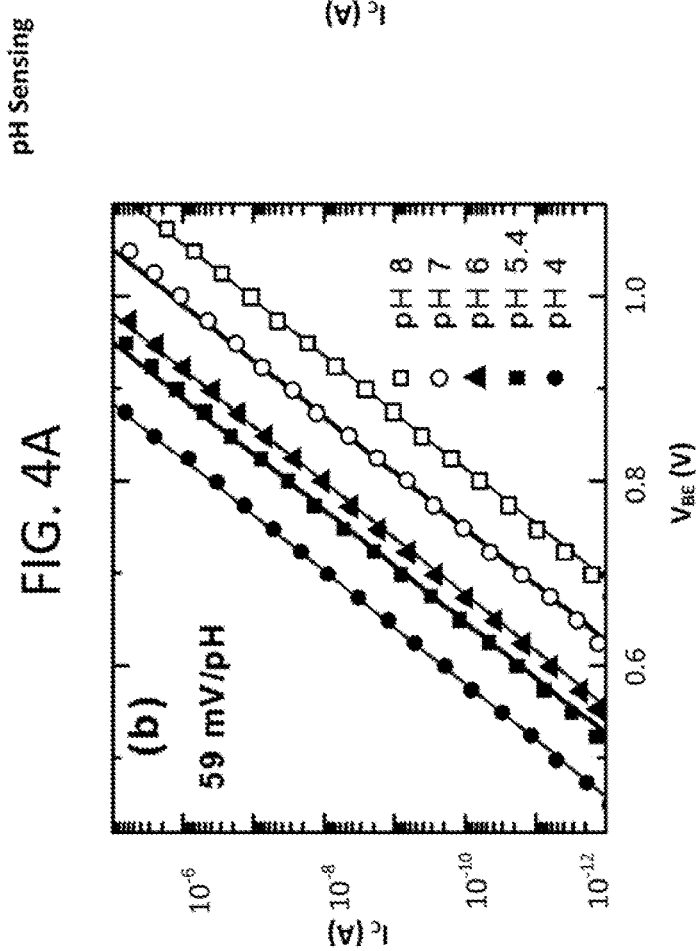

FIGS. 4A-4B consist of a plurality of charts illustrating the sensitivity of an example heterojunction bipolar transistor-based biosensor that is configured as a pH sensor. In particular, FIG. 4A plots the measured collector current (i.e., sensing current) of the example HBT-based biosensor against the base-to-emitter voltage ($V_{BE}$); and FIG. 4B plots the measured collector current against the measured pH.

As discussed above, the collector current $I_C$ is the sensing current. The base-to-emitter voltage, $V_{BE}$, is defined as $V_{BE}=V_B-V_E$, where $V_B$ is the voltage applied to the base or reference electrode (e.g., electrode 124 in FIG. 1) and $V_E$ is the voltage applied to the emitter electrode (e.g., electrode 118 in FIG. 1). The collector current is measured by varying the voltage applied to the emitter electrode and setting the voltage applied to the reference electrode and the voltage applied to the collector electrode (e.g., electrode 110 in FIG. 1) to zero. The curve illustrating the collector current reversibly shifts by approximately fifty nine mV/pH; this implies a limit to the pH sensitivity.

FIG. 4B plots values for the collector current that are measured at a fixed base-to-emitter voltage (measured as a function of the pH of the aqueous solution). As illustrated, the change in collector current is tenfold for a corresponding unit change in pH. This indicates that the biosensor is highly sensitive to pH.

Although various embodiments which incorporate the teachings of the present invention have been shown and described in detail herein, those skilled in the art can readily devise many other varied embodiments that still incorporate these teachings.

What is claimed is:

1. A sensor, comprising:
    a heterojunction bipolar transistor, comprising:
        a semiconductor collector including a collector electrode for connecting to a collector voltage;
        a semiconductor base disposed on the semiconductor collector, wherein the semiconductor base is formed from a first semiconductor material; and
        a semiconductor emitter disposed on the semiconductor base and including an emitter electrode for connecting to an emitter voltage, wherein the semiconductor emitter is formed from a second semiconductor material different from the first semiconductor material;
    a sensing surface, wherein the sensing surface comprises:
        a conducting film, wherein the conducting film has an area that is larger than an area of the semiconductor emitter; and
        a reference electrode; and
    an extended base component connecting the semiconductor base to the sensing surface.

2. The sensor of claim 1, wherein the first semiconductor material is silicon germanium.

3. The sensor of claim 1, wherein the second semiconductor material is polysilicon.

4. The sensor of claim 1, wherein the second semiconductor material is gallium arsenide.

5. The sensor of claim 1, wherein the conducting film has a thickness of greater than one hundred nanometers.

6. The sensor of claim 1, wherein the sensor is configured to sense a pH of an aqueous solution, and the conducting film comprises titanium nitride that is stoichiometric and contains no impurities.

7. The sensor of claim 1, wherein the sensor is configured to detect biomolecules in an aqueous solution, and the conducting film comprises a functionalized conducting metal.

8. The sensor of claim 1, wherein the sensor is configured to detect chloride ions in an aqueous solution, and the conducting film comprises a silver film coated with a monolayer of silver chloride, where the monolayer of silver chloride is positioned to directly contact the aqueous solution.

9. The sensor of claim 1, wherein the sensor is configured to detect thiolated bio-molecules in an aqueous solution, and the conducting film comprises gold metal.

10. The sensor of claim 1, wherein the extended base component comprises:
    a bond pad coupled to the semiconductor base; and
    a conducting wire coupling the bond pad to the conducting film.

11. The sensor of claim 10, wherein the bond pad comprises silicon that has been silicided at the top.

12. The sensor of claim 1, wherein the extended base component comprises:
    a bond pad coupled to the semiconductor base, wherein the conducting film is deposited directly over the bond pad.

13. The sensor of claim 1, wherein the heterojunction bipolar transistor is configured as an NPN device.

14. The sensor of claim 1, wherein the heterojunction bipolar transistor is configured as an PNP device.

15. The sensor of claim 1, wherein the semiconductor collector and the semiconductor base have opposite dopant polarities.

16. The sensor of claim 15, wherein the semiconductor emitter and the semiconductor base have opposite dopant polarities.

17. A sensor, comprising:
    a heterojunction bipolar transistor, comprising:
        a semiconductor collector including a collector electrode for connecting to a collector voltage;
        a semiconductor base disposed on the semiconductor collector, wherein the semiconductor base is formed from a first semiconductor material; and
        a semiconductor emitter disposed on the semiconductor base and including an emitter electrode for connecting to an emitter voltage, wherein the semiconductor emitter is formed from a second semiconductor material different from the first semiconductor material;
    a sensing surface, wherein the sensing surface comprises:
        a conducting film; and
        a reference electrode; and
    an extended base component connecting the semiconductor base to the sensing surface, wherein the extended base component comprises:
        a bond pad coupled to the semiconductor base, wherein the bond pad comprises silicon that has been silicided at the top; and
        a conducting wire coupling the bond pad to the conducting film.

* * * * *